United States Patent
Chen et al.

(10) Patent No.: US 10,416,113 B2
(45) Date of Patent: Sep. 17, 2019

(54) DETECTION OF REFRIGERANT CONTAMINANTS

(71) Applicant: Carrier Corporation, Farmington, CT (US)

(72) Inventors: Lei Chen, South Windsor, CT (US); Zhiwei Yang, South Windsor, CT (US); Antonio M. Vincitore, South Windsor, CT (US); Michael L. Perry, Glastonbury, CT (US); Warren Clough, Cicero, NY (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 145 days.

(21) Appl. No.: 15/505,015

(22) PCT Filed: Aug. 20, 2015

(86) PCT No.: PCT/US2015/046093
§ 371 (c)(1),
(2) Date: Feb. 17, 2017

(87) PCT Pub. No.: WO2016/029005
PCT Pub. Date: Feb. 25, 2016

(65) Prior Publication Data
US 2017/0269027 A1 Sep. 21, 2017

Related U.S. Application Data

(60) Provisional application No. 62/039,781, filed on Aug. 20, 2014.

(51) Int. Cl.
*G01N 27/40* (2006.01)
*G01N 27/416* (2006.01)
(Continued)

(52) U.S. Cl.
CPC ..... *G01N 27/4163* (2013.01); *G01N 27/4045* (2013.01); *G01N 27/4074* (2013.01); *G01N 27/4075* (2013.01); *G01N 33/0036* (2013.01)

(58) Field of Classification Search
CPC .......... G01N 27/4163; G01N 27/4074; G01N 27/4075; G01N 27/4045; G01N 33/0036
See application file for complete search history.

(56) References Cited

U.S. PATENT DOCUMENTS

| 1,864,544 A | 6/1932 | Lamb |
| 1,915,965 A | 6/1933 | Williams |

(Continued)

FOREIGN PATENT DOCUMENTS

| CN | 1734262 A | 2/2006 |
| GB | 346744 | 4/1931 |

(Continued)

OTHER PUBLICATIONS

AHRI, Air Conditioning, Heating, and Refrigeration Institute; "AHRI White Paper: Reports of R-134a Contaminated with R-40 and Other Refrigerants"; 5 pgs.

(Continued)

*Primary Examiner* — J. Christopher Ball
(74) *Attorney, Agent, or Firm* — Cantor Colburn LLP (57) ABSTRACT

A gas sensor for detecting one or more contaminants in a refrigerant includes a housing having disposed therein a membrane electrode assembly comprising a sensing electrode, a counter electrode, and a solid polymer electrolyte disposed between the sensing electrode and the counter electrode. The sensing electrode comprises nanoparticles of a first catalyst comprising noble metal. The counter electrode comprises nanoparticles of a second catalyst comprising noble metal. The sensing electrode in the sensor has been preconditioned by exposure under a positive voltage bias to (Continued)

a preconditioning gas comprising the contaminant(s) or their precursors or derivatives.

18 Claims, 4 Drawing Sheets

(51) Int. Cl.
G01N 27/404 (2006.01)
G01N 33/00 (2006.01)
G01N 27/407 (2006.01)

(56) References Cited

U.S. PATENT DOCUMENTS

| | | | |
|---|---|---|---|
| 5,173,166 | A | 12/1992 | Tomantschger et al. |
| 5,284,569 | A | 2/1994 | Lee et al. |
| 6,170,318 | B1 | 1/2001 | Lewis |
| 7,487,662 | B2 | 2/2009 | Schabron et al. |
| 7,728,978 | B2 | 6/2010 | Zhou et al. |
| 7,779,668 | B2 | 8/2010 | Leck et al. |
| 8,058,070 | B2 | 11/2011 | Minor et al. |
| 8,070,355 | B2 | 12/2011 | Minor et al. |
| 2008/0185297 | A1 | 8/2008 | Chow et al. |
| 2013/0153442 | A1* | 6/2013 | Chen ............ G01N 27/4045 205/786.5 |
| 2013/0340447 | A1 | 12/2013 | Koldewey et al. |
| 2015/0153442 | A1 | 6/2015 | Scott et al. |

FOREIGN PATENT DOCUMENTS

| | | |
|---|---|---|
| JP | 59120946 | 7/1984 |
| WO | 0114868 A2 | 3/2001 |

OTHER PUBLICATIONS

International Preliminary Report on Patentability regarding related PCT App. No. PCT/US2015/046093; dated Mar. 2, 2017; 8 pgs.
Neutronics, Inc., "Neutronics completes development of refrigrant analyzer for R40 contaminant detection in R134a systems"; Aug. 16, 2012; 2 pgs.

* cited by examiner

DETECTION OF REFRIGERANT CONTAMINANTS

CROSS-REFERENCES TO RELATED APPLICATIONS

This is a national stage of International Patent Application Serial No. PCT/US2015/046093, filed Aug. 20, 2015, which claims the benefit of U.S. provisional application No. 62/039,781, filed Aug. 20, 2014, both of which are incorporated herein by reference in their entirety.

BACKGROUND

In the field of cooling and heating, chlorinated hydrocarbons (chlorofluorocarbon, CFC) such as R11 (trichlorofluoromethane) and R12 (dichlorodifluoromethane) have been largely eliminated due to their adverse impact on the earth's ozone layer. Chlorinated fluorocarbons were initially replaced with hydrochlorofluorocarbons such as R22 (chlorodifluoromethane); however, continued concerns with their ozone depleting potential (ODP) and new concerns with the compounds' global warming potential (GWP) has led to their replacement with fluorinated hydrocarbons like R134a (1,1,1,2-tetrafluoroethane) or R32 (difluoromethane). Currently, R134a is used widely in both stationary and mobile refrigeration systems. Continued concerns with GWP, coupled with performance requirements in vapor compression heat transfer systems, have led to the development of new refrigerants such as fluorinated unsaturated hydrocarbons (i.e., fluorinated olefins) like trans-1,333-tetrafluoropropene (R1234ze).

Although chlorine-containing refrigerants have been discontinued by the mainstream refrigeration supply industry, they continue to be available through alternative distribution channels. Some of these compounds are used legitimately in applications such as chemical manufacturing and processing, laboratory use, and other non-refrigerant applications, or for limited use in older HVAC and refrigeration systems that are not compatible with newer refrigerants, they are also used illegitimately as a substitute for non-chlorinated refrigerants in systems that are designed for non-chlorinated refrigerants. Counterfeit refrigerants containing varying amount of ozone-depleting chlorinated substances make them illegal in certain parts of the world under the terms of the Montreal Protocol. One of the counterfeit refrigerant compositions that has drawn serious concern is methylchloride (R40) because of its flammability and deleterious interaction with the materials in refrigeration systems. There have been a number of reported accidents due to R40 being used as R134a or R134a contaminated by R40, resulting in HVAC or refrigeration system failures or serious human injuries. Specifically, the flammability of R40 can present unexpected risks for the operators maintaining refrigeration systems when improperly used as R134a. Moreover, many systems designed for use with R134a contain aluminum components, with which R40 can react to produce pyrophoric substance trimethyl aluminum that spontaneously ignites in air, creating a serious fire or explosion hazard. Other potential contaminants include R12 and R22 (chlorodifluoromethane). R152a (1,1-difluoroethane), although it does not contain chlorine, is also a contaminant of concern due to its flammability. Though contaminated refrigerants have been found in mobile air conditioners, stationary air conditioning systems and transport refrigeration systems in many countries, R40 has been identified to be the most detrimental. It is unknown what the lowest allowable concentration of R40 is in a refrigeration system without causing system failure; however, AHRI standard 700-2012, specifications of fluorocarbon refrigerants, would allow up to 0.5% of volatile impurities. Therefore, there is an urgent need of accurate detection technologies to identify R40 of low concentrations (as low as 0.5%) to prevent it from entering those systems. In view of the above, it would be desirable to have the capability to quantify contaminants, particularly R40, in refrigerants such as R134a.

Various types of sensors have been proposed for detecting contaminants in refrigerants. These include gas chromatograph/mass spectrophotometers (GC/MS), infrared analyzers, halide torching testers, etc. However, many such sensors have limitations that can impact their effectiveness. For example, GC/MS is highly accurate, but is expensive and not readily portable, rendering it unsuitable for deployment in the field for use with refrigerant systems. Portable infrared detectors have shown a detection limit in ca. 3% that is inadequate for preventing lower concentration R40 to be identified. Current IR detectors not specifically designed to address R40 can also produce false positive outcome. Halide torch testing can distinguish between chlorinated species and non-chlorinated species with extremely high sensitivity ca. 300 ppm; however, it is prone to false alarm because of the ultra-sensitivity and incapable of discern R40 from other relatively benign chlorinated contaminants.

In view of the above, there remains a need for new detection alternatives that may provide sensitivity to low contaminant levels and a robust response to eliminate false alarms, and be properly designed to make affordable detectors available for field deployment particularly mobile air conditioners and transport refrigeration systems.

BRIEF DESCRIPTION

According to some aspects of this disclosure, a gas sensor for detecting one or more contaminants in a refrigerant includes a housing having disposed therein a membrane electrode assembly comprising a sensing electrode, a counter electrode, and a solid polymer electrolyte disposed between the sensing electrode and the counter electrode. The sensing electrode comprises a first catalyst comprising nanoparticles that comprise noble metal. The nanoparticles of the first catalyst are unsupported or are supported on a non-carbon black support. Also, the sensing electrode in the sensor may be preconditioned by exposure under a positive voltage bias to a preconditioning gas comprising the contaminant(s) or their precursors or derivatives. The counter electrode comprises a second catalyst comprising nanoparticles that comprise noble metal. The sensor also includes a first flow field in fluid communication with a first opening in the housing to direct a flow of test refrigerant to flow by and/or through the sensing electrode. The sensor also includes first and second current collectors in electrical contact with the sensing and counter electrodes, respectively, and an electrical circuit connecting the sensing electrode and the counter electrode.

In another aspect, a method of preconditioning a sensor for the detection of contaminants in a refrigerant is provided. The sensor comprises a housing and a membrane electrode assembly disposed in the housing. The membrane electrode assembly comprises a first catalyst comprising noble metal nanoparticles that are unsupported or are supported on a non-carbon black support, a counter electrode comprising a second catalyst comprising noble metal nanoparticles, and a solid polymer electrolyte disposed between the sensing electrode and the counter electrode. A first current collector is in electrical contact with the sensing electrode, and a second current collector is in electrical contact with the counter electrode. A first flow field is in fluid communication with a first opening in the housing to direct test refrigerant to flow by or through the sensing electrode. An electrical circuit connects the sensing electrode and the counter electrode. The preconditioning method comprises applying a positive voltage bias to the sensing electrode and exposing the sensor to a preconditioning gas comprising the contaminant(s) or their precursors or derivatives.

In another aspect, a method of testing a refrigerant for contaminant(s) using the above-described sensor comprises applying a positive bias voltage to the sensing electrode relative to the counter electrode or a reference electrode, introducing the refrigerant to be tested to the first flow field, and measuring a test response voltage or current in the electrical circuit connecting the sensing electrode and the counter electrode.

BRIEF DESCRIPTION OF THE DRAWINGS

Subject matter of this disclosure is particularly pointed out and distinctly claimed in the claims at the conclusion of the specification. The foregoing and other features, and advantages of the present disclosure are apparent from the following detailed description taken in conjunction with the accompanying drawings in which:

DETAILED DESCRIPTION

Figure 1:
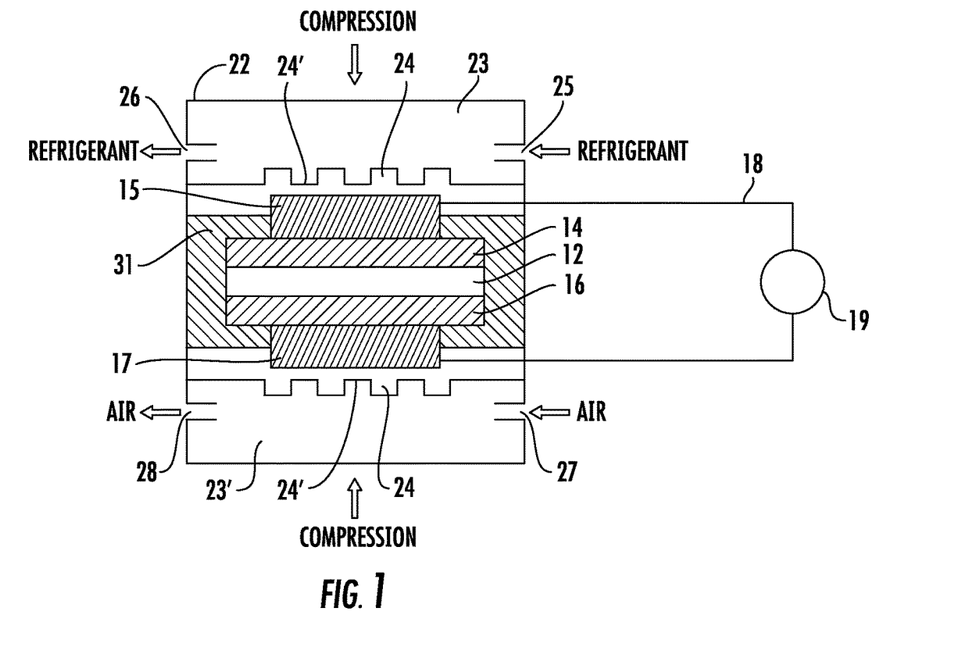
FIG. 1 depicts a simplified schematic representation of a gas sensor as described herein with both flow fields on both sensing electrode and counter electrode to direct the refrigerant to be detected and air respectively.

A gas sensor is schematically shown in FIG. 1, in which a membrane electrode assembly (MEA) has a solid polymer electrolyte (SPE) (i.e., ion conducting polymer or ion conducting polymer infiltrated porous matrix) 12 disposed between sensing electrode 14 and counter electrode 16. Current collectors/gas diffusion media 15 and 17 are attached to the electrodes and are connected to circuit 18, which includes measurement and/or control device 19. In some embodiments, an optional reference electrode (not shown) can be disposed in the SPE 12 at a location between the sensing electrode 14 and the counter electrode 16 and electrically connected to measurement and/or control device 19. Housing 22 includes flow field plates 23 and 23' with gas channels 24 and ribs 24'. The flow field plates 23 and 23', form channels 24 for refrigerant entering and exiting through openings 25 and 26 and for air entering and exiting through openings 27 and 28. The ribs 24' of the flow fields 23 and 23' are pressed against the MEA assembly to maintain electrical contact and seal around the edge of the MEA. The edges of the electrode assembly membrane are sealed against seal 31 formed of a seal material such as rubber so that the test gas and reference gas are maintained on opposing sides of the MEA and the sensing electrode 14 and the counter electrode 16 are electrically isolated, although other techniques known in the art (e.g., disposing the MEA in a frame (not shown) that is sealed to the edges of the housing) can be used. The current collectors 15, 17 can be formed from a conductive mesh or felt, and are depicted with thickness so that they can also function as gas diffusion media for the refrigerant tested and reference gas (i.e. air) to reach the surface of the electrodes 14, 16. In other embodiments, the current collectors 15, 17 can be relatively thin, almost 2-dimensional conductive screens on the surface of the electrodes 14, 16 with adjacent porous gas diffusion media (not shown) that does not have to be conductive. The current collector/gas diffusion medium 15 associated with the sensing electrode 14 can be formed from an oxidation-resistant material such as graphitized carbon or stainless steel. The current collector/gas diffusion medium 17 can be formed from a conductive material such as carbon or stainless steel. Measurement and/or control device 19 can be a voltmeter or ampere meter, but in many cases comprise a potentiostatic circuit, microprocessor, electronic control unit (ECU), or similar electronic device with integrated voltage and or amperage measurement functions and also can apply a voltage bias between the sensing electrode 14 and counter electrode 16 during operation of the sensor.

Figure 2:
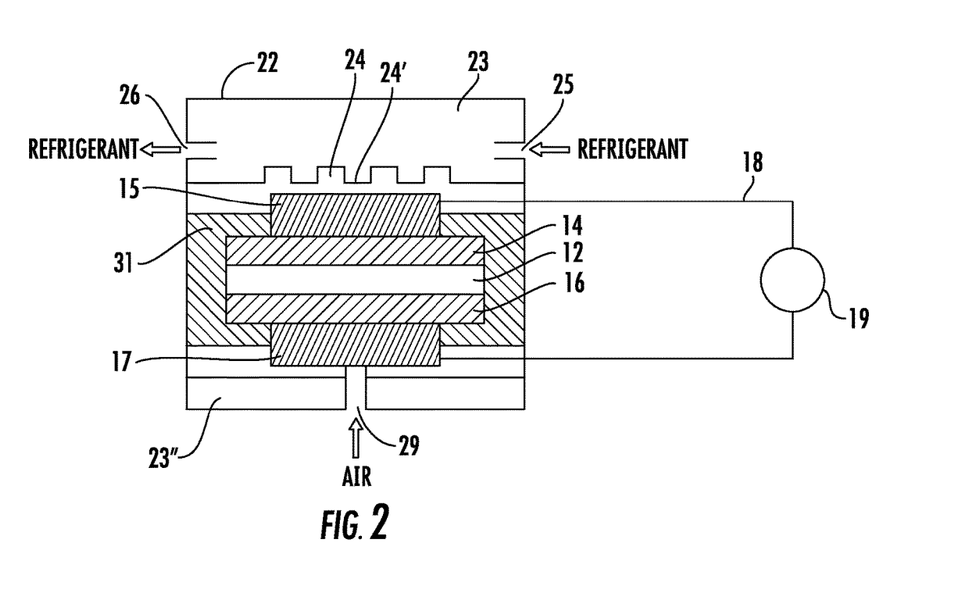
FIG. 2 depicts an alternative sensor configuration with the counter electrode exposed to unforced air via one or more opening on the associated endplate.

An alternative embodiment is shown in FIG. 2, which uses component numbering from FIG. 1 to describe like components, the description of which are not necessarily repeated below. As shown in FIG. 2, the sensor includes endplate 23 having flow channels 24 that provides a flow field on the sensing electrode to circulate a refrigerant to be tested. End plate 23", however, has only single opening 29 (and optionally additional openings) for air to diffuse through gas diffusion medium 17 to reach the counter electrode 16. The openings in FIGS. 1 and 2 are shown as completely open, although it is understood that they may be covered with a screen or gas permeable membrane. Also, the openings are shown for purposes of illustration as leading directly into the MEA, but the gas may also be introduced into interior chambers through channel(s) that lead from an outer surface of the sensor to interior chambers via expansion of the refrigerant or simply diffusion. The electrodes 14, 16 can be bonded to the solid polymer electrolyte as depicted in FIGS. 1 and 2, but can also be held together by other means such as mechanical clamps without compromising the functionalities of the sensor. In another embodiment, the housing includes a flow field to direct a flow of the refrigerant to be tested to flow by or through the sensing electrode and an opening in fluid communication with the counter electrode for air to contact the counter electrode.

Figure 3A:
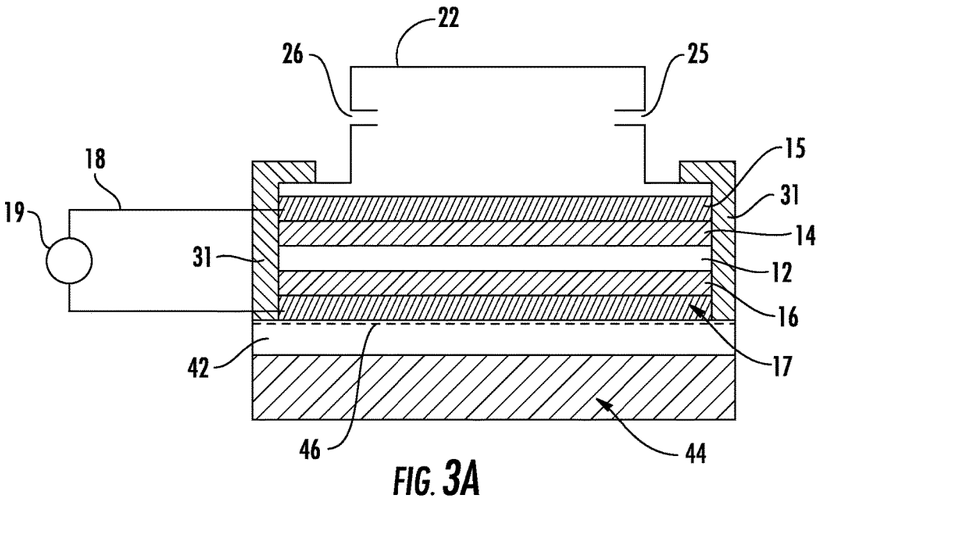
FIGS. 3A and 3B depict an alternative sensor configuration with the counter electrode chamber sealed against ambient air and humidity control liquid disposed therein.
Figure 3B:
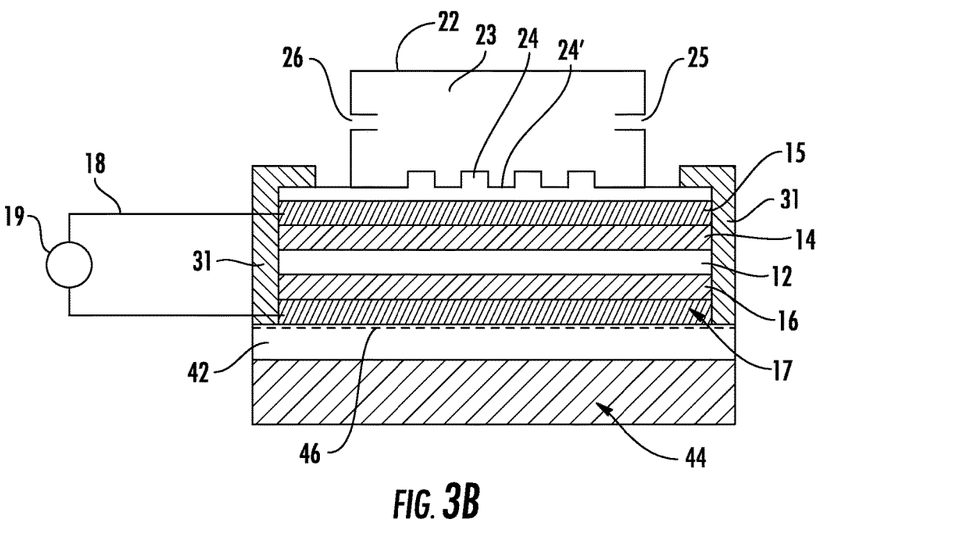

An alternative embodiment is shown in FIGS. 3A and 3B, which uses component numbering from FIGS. 1 and 2 to describe like components, the description of which is not necessarily repeated below. FIGS. 3A and 3B depict an exemplary embodiment where the counter electrode is not exposed to air or ambient gas, but is instead exposed to sealed chamber 42, which also contains a liquid material such as an aqueous salt or acid solution 44, which can be isolated from contact with the counter electrode 16 by a gas-permeable membrane 46. FIG. 3A does not depict the details of a first flow field associated with the sensing electrode 14 and current collector/gas diffusion media 15; however, FIG. 3B depicts an exemplary flow field plate 23 having channels 24 and ribs 24' configured similarly to FIGS. 1 and 2.

Of course, the embodiments depicted in FIGS. 1-3 are schematic and exemplary in nature, and other configurations can be used as well. Exemplary gas sensor configurations and variations thereon are disclosed, for example, in U.S. Pat. No. 5,650,054, 5,573,648, 6,200,443, 6,948,352, US 2009/0184005 A1, and US 2010/0012494 A1, the disclosures of which are incorporated herein by reference in their entirety.

Although the disclosure is not bound by any theory or perceived mechanism of operation, electrochemical oxidation of methyl chloride may take place via a one-electron process as shown in equation (1) below, with concomitant reaction at the counter electron as shown in equation (2):

$$ClCH_3+H_2O-e^-=O=CH_2+HCl+H^+ \quad (1)$$

$$\tfrac{1}{2}O_2+2H^++2e^- \rightarrow H_2O \quad (2)$$

The precise composition of the electrodes, and materials used in fabricating them, will depend on the particular hydrocarbons being tested for and on design parameters for the sensor and other system components with which it is used. A variety of catalytic noble metals and alloys (e.g., iridium, rhenium, palladium, platinum, copper, indium, rubidium, silver, gold) can be used to form the electrodes. In some exemplary embodiments, the sensing and/or counter electrodes comprise platinum or a binary or ternary platinum alloy such as PtNi, PtFe, PtCo, PtRu, PtRuNi, PtCr, PtCoCr, PtIrCo, or PtCuFe, wherein the Pt content in atomic ratio ranges from 20% to 100%. In some palladium, or a mixture or alloy of platinum and palladium. In some exemplary embodiments, the sensing and/or counter electrodes comprise palladium or a palladium alloy such as PdAg, PdNi, PdCu, PdRu, or PdY, wherein the Pd content in atomic ratio ranges from 30% to 100%.

The counter electrode also comprises a catalyst comprising noble metal, which can be the same as or different than the composition of the noble metal catalyst of the sensing electrode. The catalysts in the counter electrode can be chosen to specifically facilitate oxygen reduction reaction.

Figure 4:
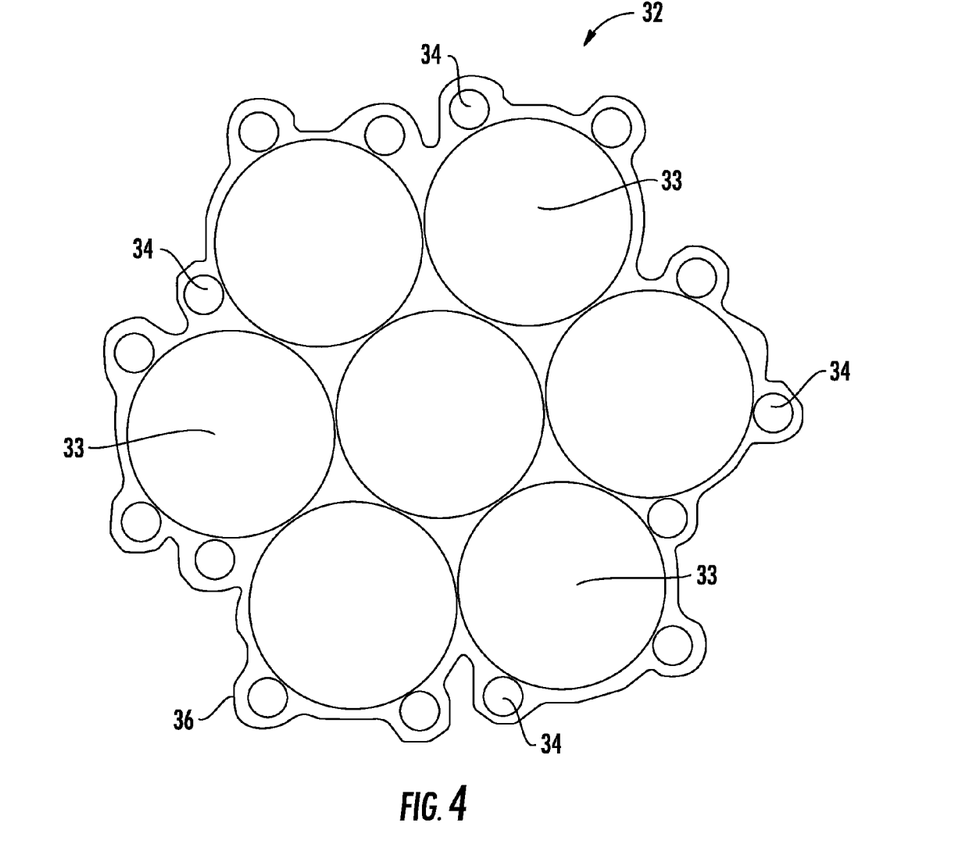
FIG. 4 depicts an exemplary supported catalyst as described herein.

Electrodes used in electrochemical sensors typically include an electrically conductive material in addition to the noble metal catalyst, and this is often provided by disposing particles of noble metal catalyst on larger particles of carbon, which is commonly referred to as a carbon-supported catalyst. However, for the detection of hydrocarbons or CFCs or HCFCs involving oxidation of the hydrocarbons and substituted hydrocarbons on the sensing electrode, it was discovered that the voltage potentials needed to effectively oxidize hydrocarbons such as methylchloride exceeded the thermodynamic oxidation of carbon support materials, (e.g, 207 mV vs. standard hydrogen electrode). Accordingly, the catalyst in the sensing electrode of the sensors described herein is unsupported or is supported on an oxidation-resistant support. In the case of unsupported catalyst, the sensing electrode can be applied 'neat' onto the solid polymer electrolyte by forming an ink comprising nanoparticles (by nanoparticles, it is meant that the particles have a nominal diameter of less than 20 nm, more specifically from 2-10 nm) and ionomer dispersed in a solvent mixture, and depositing a layer of the ink onto the surface of the solid polymer electrolyte by screen printing, ink jet printing, or similar methods. After evaporation of the solvent, the resultant electrode is in the form of a layer having a composite structure comprising catalyst nanoparticles in an ionomer matrix, where the ionomer functions as a conductive matrix material having catalyst nanoparticles dispersed throughout. A second method to fabricate MEAs is to deposit the electrode ink onto a substrate, i.e. Teflon™ or Kapton™ sheet, to make a decal after solvent evaporation, followed by a hot pressing to transfer the catalyst layer onto a membrane. In the case of a supported catalyst for the sensing electrode, the catalyst is supported on an oxidation-resistant conductive support, which can comprise oxidation-resistant support particles that are typically larger than the catalyst nanoparticles. In some exemplary embodiments, the support particles can have a nominal diameter of from 20 to 200 nm. A supported catalyst is depicted in FIG. 4, which depicts a portion of an agglomerate 32 having conductive support particles 33 with catalyst particles 34 disposed thereon, covered by a thin layer of ionomer 36. By "oxidation-resistant, it is meant that at the operational positive voltage bias of the sensor (i.e., 100 to 400 mV), the material of the support particles produces a baseline signal less than $\tfrac{1}{5}^{th}$ of the signal generated by a refrigerant contaminant such as R40. Examples of materials for the oxidation-resistant support in the sensing electrode include, but are not limited to graphitized carbon, carbon nanotubes (CNT), and conductive metal oxides such as $TiO_2$, $WO_3$, $SnO_2$, etc. In another embodiment, the noble metal containing catalyst and conductive oxides can be co-loaded onto a support to achieve higher activity, for example Pt—$WO_3$/CNT. These conductive metal oxides can be undoped or they can be doped with metals such as Sb, V, Tl, Mn, Co, Fe, etc.

As mentioned above, the sensing electrode in the sensor can be preconditioned by exposure under a positive voltage bias to a preconditioning gas comprising the contaminant(s). This preconditioning may help to provide selectivity between the response of the sensor to refrigerants like R134a and the response to contaminants like R40, and/or the preconditioning may help to provide more accurate and reliable response to contaminants like R40. The compounds used for preconditioning can include contaminants likely to be encountered in the field, including but not limited to R40, R12, R22, or R152a. The preconditioning can utilize a single contaminant of interest or mixtures of contaminants of interest. Additionally, the preconditioning can be performed with gaseous contaminant(s) in the refrigerant (e.g., R134a) or in air or other carrier gases such as nitrogen. Concentrations of the contaminant(s) in refrigerant, air, or other carrier gases can range from 0.5 vol. % to 50 vol. %. The preconditioning can be performed with a single continuous exposure or with pulsed or periodic exposures. The duration of the preconditioning can vary depending on the specific design parameters of the sensor and the contaminant(s) being preconditioned for, and is preferred to continue until a stable response is attained at the sensing electrode. For example, cyclic exposure under positive voltage bias for 3-10 minutes every 1 hour to the selected chemicals, until a stable, unvarying response is measured in the electrical circuit connecting the sensing electrode and the counter electrode. Also, depending on the specific design parameters of the sensor and the contaminant(s) being preconditioned for, the sensitivity of the sensor could be further enhanced by subjecting the sensor to positive voltage bias while exposing the sensing electrode to air under ambient temperature and constant or controlled humidity. This exposure can be provided for extended periods, e.g., two days to two weeks or longer, and can be accomplished by maintaining the sensing electrode under positive voltage bias while the sensor is in an idle state. The counter electrode can also be exposed to either ambient air or humidity regulated air for further conditioning. In some embodiments, humidity can be controlled with a humidity control agent disposed in or adjacent to the counter electrode. Exemplary humidity control agents include salts or acids, such as $MgCl_2$, LiCl, NaBr, $CH_3COOK$, $MgNO_3$, or sulfuric acid, disposed in the liquid phase of an exemplary sensor constructed as illustrated in FIG. 3. The positive voltage biases used for the preconditioning can be those such as described below for operation of the sensor.

The counter electrode can be formed from non-supported catalyst and/or conventional catalyst on carbon with catalyst particles supported on carbon particles with conductive or non-conductive binders, and the current collector associated with the counter electrode can also be formed from a carbon fiber screen, mesh, or felt. In an exemplary embodiment, the counter electrode can be formed from an agglomerate of a conductive carbon support particles with a nominal diameter of about 20-200 nm, with catalyst particles (nominal diameter of about 2-10 nm) disposed thereon, covered by a thin layer of binder (e.g., an ionomer such as Nafion™ or a nonconductive binder), shown in FIG. 4.

The solid polymer electrolyte can be formed from any ionomer capable of conducting ions across the electrolyte membrane between the sensing electrode and counter electrode. Exemplary ionic polymers include ionic groups attached to a polymer so that the polymer has the ionic-exchange ability, such groups including but not limited to sulfonic acid, phosphonic acid, and sulfonimide acid. Exemplary ionomers include per-fluorinated sulfonic acid ("PFSA"), such as Nafion™ ionomer and Solvey Solexis Auqivion™ ionomer, sulfonated polystyrene, sulfonated polysulfone, disulfonated poly(arylene ether sulfone) block-copolymers ("BPSH"). Conventional additives, e.g., surfactants, solvents (e.g., polyethylene glycol), and fine particles (such as functionalized of non-functionalized silica, carbon-based powders, metal-oxides particles) can also be added to the polymer matrix. The above-described ionomers for the solid polymer electrolyte can also be used as the ionomer for the electrodes.

In some embodiments, the solid polymer electrolyte and/or ionomer in the electrodes can be impregnated with a polar liquid such as water or an ionic liquid (i.e., a salt above its melting point). However, the positive voltage bias needed to oxidize hydrocarbons and substituted hydrocarbons can cause water to be subject to electrolysis promoted by the catalyst, and ionic liquids can contribute to noise ratios in the electrical circuit connecting the sensing and counter electrodes that can interfere with signal measurement. Accordingly, in some exemplary embodiments, the membrane electrode assembly is free of ionic liquid. In some embodiments, the membrane electrode assembly is free of water or is partially saturated with water, except for the presence of water that is electrochemically generated at the counter electrode by reaction (2) described above.

The sensor can be operated by applying a positive bias voltage to the sensing electrode relative to the counter electrode or a reference electrode, exposing the sensing electrode to the gas being tested, measuring voltage or current in an electrical circuit connecting the sensing electrode and the counter electrode, and converting the measured voltage or current to a reading indicative of the presence and/or concentration of the component in the gas being tested. In some embodiments, a baseline response is determined by exposing the sensing electrode to pure refrigerant (e.g., R134a) under positive voltage bias for 1-10 minutes, or longer, and this baseline response can be subtracted from the later measured response to determine the quantity of contaminant(s) in the refrigerant being tested. Oxidation of hydrocarbons or substituted hydrocarbons at the sensing electrode will cause an electrochemical response that can be detected as voltage or current in the circuit. In some embodiments, the potentiostatic circuit, microprocessor, or similar device 19 is configured to apply the positive voltage bias and measure the response voltage or current. In some embodiments, the positive voltage bias applied to the sensing electrode relative to the counter electrode or reference is from 20 mV to 700 mV. In some embodiments, the applied positive voltage bias can be applied as a positive voltage bias ranging from 200 mV to 400 mV.

Further description is provided in the following examples.

EXAMPLES

Figure 5:
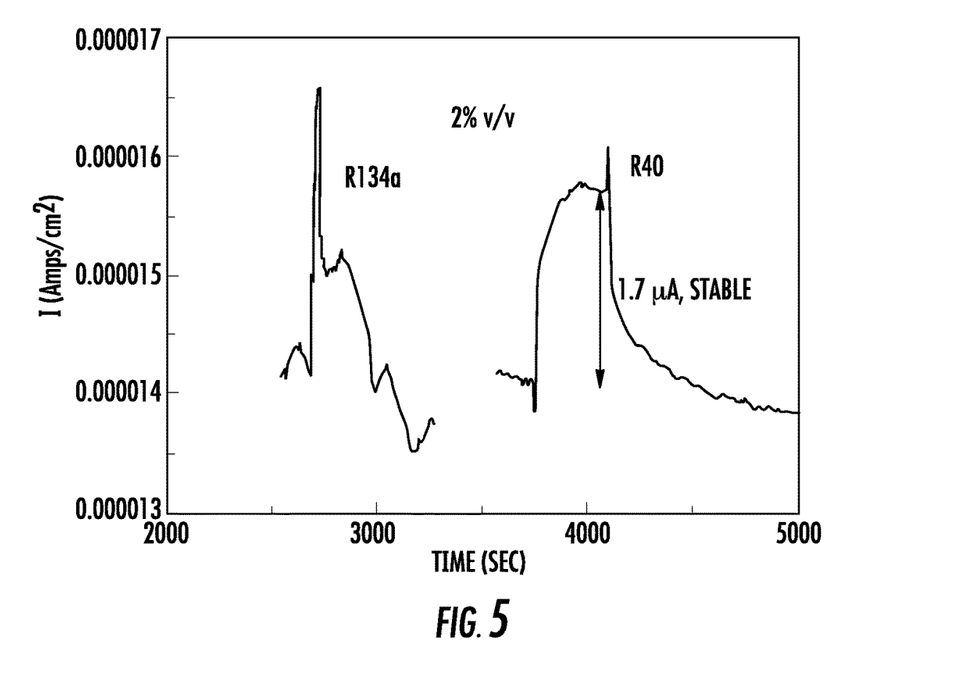
FIG. 5 depicts exemplary output of a sensor as described herein in response to sequential exposures to R134a and R40 during sensor pre-conditioning.

A prototype sensor configured as shown in FIG. 1 was operated with a positive voltage bias of 200 mV at the sensing electrode relative to the counter electrode exposed to air, where R134a and R40 were flown through the sensing electrode via a flow field respectively. The sensor response is shown in FIG. 5. As shown in FIG. 5, the sensor effectively distinguished between R134a and R40 by the characteristics of the signal response. R134a produced a sharp spiked peak response followed by a rapid diminishing response, whereas R40 produced a sustainable response with minimal signal attenuation prior to the termination of gas flow manifested by the dropping off of the signal.

Figure 6:
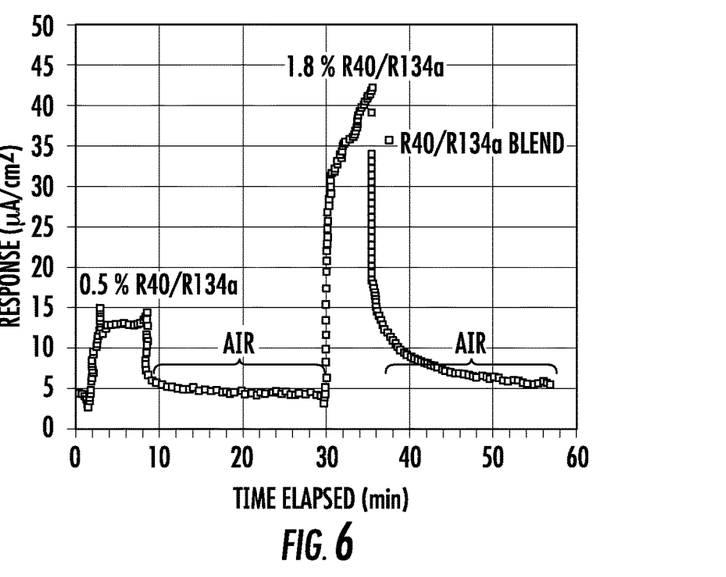
FIG. 6 depicts output of a sensor as described herein in response to exposures to R134a contaminated with R40.

In another example, a preconditioned prototype sensor was exposed to samples of R134a blended in with 0.5 vol. % and then 1.8 vol. % of R40 as a contaminant. The results are shown in FIG. 6. As shown in FIG. 6, the sensor effectively identified the presence of R40 with a plateau response, which increased with increased concentration of R40.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions or equivalent arrangements not heretofore described, but which are commensurate with the spirit and scope of the present disclosure. Additionally, while various embodiments of the present disclosure have been described, it is to be understood that aspects of the present disclosure may include only some of the described embodiments. Accordingly, the present disclosure is not to be seen as limited by the foregoing description, but is only limited by the scope of the appended claims.

The invention claimed is:

1. A method of preconditioning for the detection of contaminants in a refrigerant sensor comprising a housing, a membrane electrode assembly disposed in the housing, the membrane electrode assembly comprising a first catalyst comprising noble metal nanoparticles that are unsupported or are supported on a non-carbon black support, a counter electrode comprising a second catalyst comprising noble metal nanoparticles, and a solid polymer electrolyte disposed between the sensing electrode and the counter electrode, a first current collector in electrical contact with the sensing electrode, a second current collector in electrical contact with the counter electrode, a first flow field in fluid communication with a first opening in the housing to direct test refrigerant to flow by or through the sensing electrode, the housing including a chamber to which the counter electrode is exposed, and an electrical circuit connecting the sensing electrode and the counter electrode, the method comprising applying a positive voltage bias to the sensing electrode and exposing the sensor to a preconditioning gas comprising the contaminant(s) or their precursors or derivatives.

2. The method of claim 1, wherein the counter electrode chamber is sealed from ambient air by a seal.

3. The method of claim 1, wherein the counter electrode chamber includes an opening in fluid communication with ambient air.

4. The method of claim 1, wherein the sensor includes a second flow field in fluid communication with the counter electrode chamber to direct air to flow by or through the counter electrode.

5. The method of claim 1, wherein either or both of the sensing electrode and the counter electrode further comprise an ionomer.

6. The method of claim 1, wherein the refrigerant is a fluorinated hydrocarbon.

7. The method of claim 6, wherein the refrigerant is R134a.

8. The method of claim 1, wherein the contaminant(s) comprise a chlorine-substituted hydrocarbon.

9. The method of claim 1, wherein the contaminant(s) comprise R40, R12, R22, R142b, R143a, R125 or R152a.

10. The method of claim 1, wherein the preconditioning gas comprises the contaminant(s) and the refrigerant.

11. The method of claim 1, wherein the preconditioning gas comprises the contaminant(s) and air.

12. The method of claim 1, wherein the preconditioning gas comprises from 0.5 vol. % to 50 vol. % of the contaminant(s) based on the total volume of preconditioning gas.

13. The method of claim 1, further comprising preconditioning the sensor by exposure to controlled humidity.

14. The method of claim 1, wherein humidity is controlled by a humidity control agent disposed in or adjacent to the counter electrode.

15. The method of claim 1, wherein the noble metal catalysts comprise platinum or an alloy of platinum with one or more of ruthenium, nickel, iron, cobalt, iridium or palladium, wherein the Pt content in atomic ratio ranges from 20% to 100%.

16. A method of testing a refrigerant for contaminant(s) using the sensor of claim 1, comprising applying a positive bias voltage to the sensing electrode relative to the counter electrode or a reference electrode, and introducing the refrigerant being tested to the first flow field, and measuring a test response voltage or current in the electrical circuit connecting the sensing electrode and the counter electrode, and further comprising, prior to introducing the test refrigerant to the first flow field, applying a positive bias voltage to the sensing electrode relative to the counter electrode or a reference electrode, introducing humidity controlled air into the sensing electrode and the counter electrode, measuring a response voltage or current in the electrical circuit connecting the sensing electrode and the counter electrode, and continuing the positive voltage bias and introduction of humidity controlled air until the a stable voltage or current response is achieved.

17. A method of testing a refrigerant for contaminant(s) using the sensor of claim 1, comprising applying a positive bias voltage to the sensing electrode relative to the counter electrode or a reference electrode, and introducing the refrigerant being tested to the first flow field, and measuring a test response voltage or current in the electrical circuit connecting the sensing electrode and the counter electrode, and, further comprising, prior to introducing the test refrigerant to the first flow field, introducing a reference refrigerant with a purity of at least 99.5 vol % to the first flow field while applying a positive bias voltage to the sensing electrode relative to the counter electrode or a reference electrode, measuring a baseline response voltage or current until a stable baseline response is achieved, and comparing the test response voltage or current to the baseline response voltage or current.

18. The method of claim 17, wherein the introduction of reference refrigerant under a positive voltage bias is continued for 1 to 60 minutes.

* * * * *